(12) United States Patent
Rajaiah et al.

(10) Patent No.: US 7,834,066 B2
(45) Date of Patent: Nov. 16, 2010

(54) DENTURE ADHESIVE ARTICLES

(75) Inventors: Jayanth Rajaiah, Loveland, OH (US); Elizabeth Anne Wilder, West Chester, OH (US); Mark William Hamersky, Fairfield Township, OH (US); Steven Daryl Smith, Fairfield, OH (US); Douglas Craig Scott, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 155 days.

(21) Appl. No.: 11/590,225

(22) Filed: Oct. 31, 2006

(65) Prior Publication Data
US 2007/0185234 A1 Aug. 9, 2007

Related U.S. Application Data

(60) Provisional application No. 60/735,243, filed on Nov. 9, 2005, provisional application No. 60/760,526, filed on Jan. 20, 2006, provisional application No. 60/735,088, filed on Nov. 9, 2005, provisional application No. 60/760,660, filed on Jan. 20, 2006, provisional application No. 60/735,136, filed on Nov. 9, 2005, provisional application No. 60/760,528, filed on Jan. 20, 2006, provisional application No. 60/735,135, filed on Nov. 9, 2005, provisional application No. 60/760,516, filed on Jan. 20, 2006, provisional application No. 60/734,874, filed on Nov. 9, 2005, provisional application No. 60/760,527, filed on Jan. 20, 2006, provisional application No. 60/760,711, filed on Jan. 20, 2006.

(51) Int. Cl.
A61K 6/097 (2006.01)
A61C 13/23 (2006.01)
B32B 7/12 (2006.01)

(52) U.S. Cl. .......... 523/120; 433/180; 106/35; 428/355 R; 428/355 CP

(58) Field of Classification Search ........ 523/120; 433/168.1, 180; 106/35; 428/355 R, 355 CP
See application file for complete search history.

(56) References Cited

U.S. PATENT DOCUMENTS

| | | | |
|---|---|---|---|
| 2,496,387 A | 2/1950 | Fink | |
| 4,108,823 A | 8/1978 | Yoshimura et al. | |
| 4,373,036 A | 2/1983 | Chang et al. | |
| 4,484,894 A | 11/1984 | Masuhara et al. | |
| 4,495,314 A | 1/1985 | Keegan | |
| 4,518,721 A * | 5/1985 | Dhabhar et al. | 523/120 |
| 4,632,880 A | 12/1986 | Lapidus | |
| 4,804,412 A | 2/1989 | Komiyama et al. | |
| 4,880,702 A | 11/1989 | Homan et al. | |
| 5,061,182 A | 10/1991 | Kubo et al. | |
| 5,093,387 A | 3/1992 | Schobel et al. | |
| 5,158,825 A | 10/1992 | Altwirth | |
| 5,209,777 A | 5/1993 | Altwirth | |
| 5,239,017 A | 8/1993 | Pelesko et al. | |
| 5,658,586 A | 8/1997 | Rajaiah et al. | |
| 5,700,478 A | 12/1997 | Biegajski et al. | |
| 5,750,591 A | 5/1998 | Clarke et al. | |
| 5,880,172 A | 3/1999 | Rajaiah et al. | |
| 6,149,940 A | 11/2000 | Maggi et al. | |
| 6,166,102 A * | 12/2000 | Ahn et al. | 523/120 |
| 6,197,331 B1 | 3/2001 | Lerner et al. | |
| 6,224,372 B1 | 5/2001 | Ibsen et al. | |
| 6,276,937 B1 | 8/2001 | Gasman | |
| 6,375,963 B1 | 4/2002 | Repka et al. | |
| 6,475,498 B1 | 11/2002 | Rajaiah et al. | |
| 6,503,312 B2 | 1/2003 | Altwirth | |
| 6,617,374 B1 | 9/2003 | Rajaiah et al. | |
| 7,185,484 B2 | 3/2007 | Perkins et al. | |
| 2003/0027887 A1 | 2/2003 | Rajaiah et al. | |
| 2003/0180359 A1 | 9/2003 | Vergnault et al. | |
| 2004/0028930 A1 | 2/2004 | Wong et al. | |
| 2004/0034120 A1 | 2/2004 | Patel et al. | |
| 2004/0166068 A1 | 8/2004 | Rajaiah et al. | |
| 2005/0228066 A1 | 10/2005 | Wong et al. | |
| 2006/0106128 A1 | 5/2006 | Borja | |
| 2007/0185232 A1 | 6/2007 | Rajaiah et al. | |

(Continued)

FOREIGN PATENT DOCUMENTS

DE 3715100 11/1987

(Continued)

OTHER PUBLICATIONS

Fumiaki Kawano, DDS, PhD, et al, Impact Absorption of Four Processed Soft Denture Liners as Influenced by Accelerated Aging, International Journal of Prosthodontics, vol. 10, No. 1, Jan.-Feb. 1997, pp. 55-60, United States.

(Continued)

*Primary Examiner*—Mark Eashoo
*Assistant Examiner*—Michael Pepitone
(74) *Attorney, Agent, or Firm*—Kathleen Y. Carter; Carrie M. Benjamin; Angela K. Haughey

(57) ABSTRACT

The present invention relates to a denture adhesive article comprising: a) a safe and effective adhesive amount of a water soluble denture adhesive component; b) a safe and effective amount of a component selected from the group consisting of a water soluble plasticizer, a water soluble carrier, and mixtures thereof; wherein the article is bioerodible; and wherein the article has dry tack.

11 Claims, No Drawings

U.S. PATENT DOCUMENTS

| | | |
|---|---|---|
| 2007/0129460 A1 | 8/2007 | Rajaiah et al. |
| 2007/0185233 A1 | 8/2007 | Rajaiah et al. |
| 2007/0185235 A1 | 8/2007 | Rajaiah et al. |
| 2007/0185236 A1 | 8/2007 | Rajaiah et al. |
| 2007/0185237 A1 | 8/2007 | Rajaiah et al. |

FOREIGN PATENT DOCUMENTS

| | | |
|---|---|---|
| JP | 07-178120 | 7/1985 |
| JP | 03-090145 | 4/1991 |
| JP | 2001-212160 | 8/2001 |
| JP | 2002-095681 | 4/2002 |
| JP | 2004-141553 | 5/2004 |
| WO | WO 96/25910 | 8/1996 |
| WO | WO 01/15657 A1 | 3/2001 |
| WO | WO 01/21093 A1 | 3/2001 |
| WO | WO 01/41710 A | 6/2001 |
| WO | WO 01/41711 A1 | 6/2001 |
| WO | WO 01/51009 A1 | 7/2001 |
| WO | WO 02/30317 A | 4/2002 |
| WO | WO 2004/058195 A1 | 7/2004 |
| WO | WO 2005/081935 A2 | 9/2005 |

OTHER PUBLICATIONS

Seltzer, R. Self-Adhesive Polymeric Coatings Have Nonstick Surfaces, Chemical and Engineering News, 63, No. 41, Oct. 14, 1985, pp. 44-45, United States.

* cited by examiner

DENTURE ADHESIVE ARTICLES

CROSS REFERENCE TO RELATED APPLICATION

This application claims the benefit of U.S. Provisional Application Nos.: 60/735,243 filed Nov. 9, 2005; 60/760,526 filed Jan. 20, 2006; 60/735,088 filed Nov. 9, 2005; 60/760,660 filed Jan. 20, 2006; 60/735,136 filed Nov. 9, 2005; 60/760,528 filed Jan. 20, 2006; 60/735,135 filed Nov. 9, 2005; 60/760,516 filed Jan. 20, 2006; 60/734,874 filed Nov. 9, 2005 and 60/760,527 filed Jan. 20, 2006, and 60/760,711 filed Jan. 20, 2006 the substances of which are incorporated herein by reference.

TECHNICAL FIELD

This invention relates to denture adhesive articles and in particular to improved denture adhesive articles comprising a denture adhesive component and a water soluble plasticizer or carrier, having dry tack properties.

BACKGROUND OF THE INVENTION

Ordinary removable dentures, dental plates and the like, comprise teeth mounted in a suitable plate or base. While dentures are traditionally fitted for the individual user, the fit can change over time which may result in slippage or discomfort. Denture adhesives are used to temporarily adhere the dentures to the surfaces of the oral cavity, in particular the oral mucosa. Denture adhesives are typically applied to either the denture or oral surface at the beginning of the day when the dentures are placed into the oral cavity, and the adhesives tend to bio-erode during the course of the day due to the action of saliva and chewing.

Considerable effort has been made over the years to develop improved denture adhesive products. Both synthetic and natural polymers and gums have been used alone and in combination with various adhesives and other materials in an attempt to improve hold and reduce oozing of the adhesive from under the dental plate, and to avoid messiness and difficulty of removing the residual adhesive from the mouth and dentures after use. For example, alkyl vinyl ether-maleic copolymers and salts thereof are known for providing hold in denture adhesive compositions. Such disclosures include: U.S. Pat. No. 3,003,988, Germann et al., issued Oct. 10, 1961; U.S. Pat. No. 4,980,391, Kumar et al., issued Dec. 25, 1990; U.S. Pat. No. 5,073,604, Holeva et al., issued Dec. 17, 1991; U.S. Pat. No. 5,525,652, Clarke, issued Jun. 11, 1996; U.S. Pat. No. 5,340,918, Kittrell et al., issued Aug. 23, 1994; U.S. Pat. No. 5,830,933, Synodis et al., issued Nov. 3, 1998.

In addition to adhesion, it is desirable to reduce oozing or to reduce the negative aesthetics of oozing experienced by the consumer. Oozing may occur due to seeping of the denture adhesive from under the dental plate in the oral cavity caused by a variety of factors including a low viscosity denture adhesive, use of too much denture adhesive, improper application of the denture adhesive on the denture plate, etc. When oozing occurs in the oral cavity, the denture adhesive composition is exposed to the oral cavity. Therefore, any negative taste, negative mouth-feel, or any other any other negative aesthetic associated with the denture adhesive composition may be more noticeable and objectionable to the consumer. Sources of such negative perception may include the denture adhesive polymer itself or salts of the denture adhesive polymer, including those crosslinked with zinc salts. Taste considerations are significant since denture adhesive compositions are used in the oral cavity for up to 6-7 hours or longer. Furthermore, consumers may stop using the adhesive or may tend to apply less adhesive the next time if they experience the negative perception of ooze. This may lead to decreased denture hold or decreased denture performance. This decrease in performance can mean less denture stability, denture retention, or an increase in food lodging itself under the denture prosthesis.

In accordance with the present invention, the denture adhesive composition herein will provide these improved denture adhesive properties including improved hold, fit, ease of handling, ease of application, decreased ooze, and/or improved clean up under the varied conditions of the oral cavity.

SUMMARY OF THE INVENTION

The present invention relates to a denture adhesive article comprising:
a safe and effective adhesive amount of a water soluble denture adhesive component; and
a safe and effective amount of a water soluble plasticizer or carrier;
wherein the article is bioerodible; and wherein the article has dry tack.

DETAILED DESCRIPTION OF THE INVENTION

A detailed description of essential and optional components of the present invention is given below.

DEFINITIONS

The abbreviation "cm", as used herein, means centimeter. The abbreviation "mm" as used herein, means millimeter. The abbreviation "g" as used herein, means gram.

The term "denture" and/or "denture prosthesis" as used herein refers to either the upper or lower denture, or both.

The term "denture adhesive article" and/or "article" as used herein refers to articles designed to fit, conform and adhere to contoured surfaces, such as a denture, as well as the gums or the roof of the mouth. The articles herein are substantially solid prior to use and can be picked up manually in substantially one piece and positioned on the denture.

The term "flexible" or "flexible article" as used herein means that a 0.67 mm thick piece of the article may be wrapped 180 degrees around a solid cylinder of 1 cm diameter without cracking upon visual observation.

The term "safe and effective adhesive amounts" as used herein means an amount sufficient to provide adherence to the oral cavity and/or provide adherence of a denture to the oral cavity, without toxicity to the user or damage to oral tissue.

By "safe and effective amount", as used herein, is meant an amount of an agent high enough to significantly (positively) modify the condition to be treated or positively modify the benefit sought, but low enough to avoid serious side effects (at a reasonable benefit/risk ratio), within the scope of sound medical/dental judgment. The safe and effective amount of an agent may vary with the particular condition being treated, the age and physical condition of the patient being treated, the severity of the condition, the duration of treatment, the nature of concurrent therapy, the specific form of the source employed, and the particular vehicle from which the agent is applied.

The term "AVE/MA" as used herein refers to alkyl vinyl ether-maleic acid or anhydride copolymer. The term "mixed polymer salts" or "mixed salts", as used herein, refers to salts of AVE/MA where at least 2 different cations are mixed on the same polymer with each other or with other salts.

The term "free acid" or "FA" component, as used herein, refers either to the unreacted carboxyl groups (—COOH) of AVE/MA copolymer plus any other monovalent cations of carboxyl groups (e.g., COONa) of the polymer. Monovalent cations include Group IA cations, such as sodium, potassium, hydrogen, etc. In one embodiment, the term "free acid" refers to the unreacted carboxyl groups (—COOH) of AVE/MA plus sodium and potassium cations. In another embodiment, the term "free acid" refers only to the unreacted carboxyl groups (—COOH) of the AVE/MA.

The term "toxicologically-acceptable", as used herein, is used to describe materials that are suitable in their toxicity profile for administration to humans and/or animals.

By "non-aqueous", as used herein, is meant that the article does not contain added water but may contain water that is included in another component as supplied commercially by the manufacturer.

The term "water-insoluble" as used herein refers to a material that, when exposed to an excess of water, does not dissolve, but may disperse to varying degrees. In some embodiments the term "water-insoluble" refers to a material that is less than about 10%, 5%, 2%, or 1% soluble in water.

The term "thermoplastic" as used herein refers to a material that melts, softens, and becomes more flexible, extrudable, deformable, shapable, moldable, flowable, processable, and/or changes rheology when exposed to heat. In one embodiment the material generally solidifies, hardens, and/or substantially returns to its original condition, when subsequently cooled.

The term "bioerodible" as used herein means that the article, when exposed to excess of water or saliva, will erode over time due to physical and/or chemical action. The time necessary to erode the article can be any length of time from instantaneous to five days, in one embodiment the time to erode is from about 1 to about 3 days. The article may erode completely or substantially, however ultimately the article will lose its original form and/or integrity. For example, after application and use for at least about 24 hours in the oral cavity the article will not have sufficient product integrity to easily separate or peel, in its original form, from the denture or oral surface. In one embodiment the article bioerodes such that no portion of the article remains on the denture or mouth after the article has been used in the oral cavity for about 24 hours. In another embodiment some portion or residue from the article remains on the denture or oral surface after removing the denture from the oral cavity; however, this portion or residue from the article can be cleaned by brushing away with a toothbrush, but not easily separated from the denture.

The percentages used herein to describe the cationic salt function of the alkyl vinyl ether-maleic acid or anhydride copolymers are defined as the stoichiometric percent of the total initial carboxyl groups reacted on the polymer.

All other percentages used herein are by weight of the article unless otherwise indicated.

All measurements referred to herein are made at 25° C. unless otherwise specified.

All percentages, ratios, and levels of ingredients referred to herein are based on the actual amount of the ingredient, and do not include solvents, fillers, or other materials with which the ingredient may be combined as a commercially available product, unless otherwise indicated.

All publications, patent applications, and issued patents mentioned herein are hereby incorporated in their entirety by reference. Citation of any reference is not an admission regarding any determination as to its availability as prior art to the claimed invention.

To the extent that any meaning or definition of a term in this written document conflicts with any meaning or definition of the term in a document incorporated by reference, the meaning or definition assigned to the term in this written document shall govern.

DENTURE ADHESIVE ARTICLE

The present invention relates to denture adhesive articles (e.g. shaped) designed to fit, conform and adhere to contoured surfaces such as a denture as well as the gums or the roof of the mouth.

In one embodiment the articles herein minimize or avoid the problem of premature sticking during application of the article to the denture. That is, with some prior art denture adhesive articles, before the article can be properly positioned over a target surface on the denture, inadvertent contact of the article with the denture may cause premature sticking at one or more locations on the denture. This may inhibit proper positioning of the article. Premature sticking may also cause contamination or degradation of the article prior to final positioning on the denture.

In one embodiment the term "dry tack" as used herein means that present articles exhibit minimal and/or no adhesive or cling properties in the dry state until activated by pressure applied by a user. In one embodiment this characteristic permits the present articles to be stored and dispensed in any desired mode without encountering the difficulties of premature clinging or adhering to themselves, and without the need for separate release sheets, liners, spacers, or the like. At the same time, in one embodiment when pressure activated at the desired location and at the desired time, the articles can, in the dry state, exhibit sufficient adhesive properties to form a bond to most plastic surfaces including a denture surface, this bond being sufficiently strong to survive handling of the denture without bond failure. Therefore, in one embodiment the articles herein, in the dry state, adhere to a target denture surface only when pressed thereagainst, thereby minimizing or avoiding this problem of inadvertent adherence during positioning on the denture surface. In one embodiment then, the articles herein do not have to be moistened or wet prior to application to the denture, thus providing a simple and easy way to apply an article to the denture.

In one embodiment the term "dry tack" as used herein means that present articles exhibit minimal and/or no adhesive or cling properties until activated by pressure applied by the user after the article has been warmed by the hands of the user, potentially during the course of application of the article to the denture surface.

In another embodiment the articles herein are non-tacky to the touch prior to application to the denture.

In another embodiment the term "dry tack" as used herein means articles herein in a dry and un-wetted state, are capable of immediate bonding by surface attachment to a dry plastic, polymethyl methacrylate, and/or other denture prothesis substrate, upon subjecting the article to pressure. In one embodiment the dry article, develops bonding by surface attachment to a dry denture prosthesis substrate upon the application of finger pressure whereby the article remains bonded under its own weight, and the article herein will not remain bonded to this dry substrate under its own weight without using finger pressure to apply the article to the substrate. In one embodiment the force or pressure may be generated by one or more fingers. This force or finger pressure, in one embodiment, may be applied for 1-10 seconds or longer. In another embodiment the bonding of the article to the substrate is maintained from about 10 seconds to about 3 minutes or longer, in another embodiment from about 30 seconds to about 1 minute or longer.

In one embodiment the dry tack of the article is from about 0.025, 0.1, 1, 10, 100, 1000 gram force/square centimeter to about 10, 100, 1000, 10,000, 50,000, 100,000 gram force/square centimeter and any combination thereof.

In one embodiment the dry tack of an article that can be repositioned is from about 0.025 grams/force square centimeter to about 0.30 grams/force square centimeter, and in another embodiment from about 0.025 gram force/square centimeter to about 0.25 gram force/square centimeter.

It is reported that the room temperature modulus of any tacky adhesive is less than $3 \times 10^6$ dynes/cm$^2$ when measured at a frequency of 1 Hz. This finding is a criterion for tack and has been given the name "Dahlquist criterion for tack." (Adhesion and Adhesives Technology, by Alphonsus Pocius, $2^{nd}$ Edition, 2002 Carl Hanser Verlag, Munich).

In one embodiment of the current invention, the article has a modulus greater than the 'Dahlquist criterion for tack' of about $3 \times 10^6$ dynes/cm$^2$. In another embodiment, the article has a shear storage modulus G' (measured in dynes/cm$^2$ at a frequency of about 1 Hz at about 25C.) greater than about $5 \times 10^6$; in another embodiment greater than about $1 \times 10^7$; in another embodiment greater than about $5 \times 10^7$; and in another embodiment greater than about $8 \times 10^7$.

In one embodiment the article has a shear storage modulus G' (measured in dynes/cm$^2$ at a frequency of about 1 Hz at about 25C.) from about $1 \times 10^6$, $3 \times 10^6$, $5 \times 10^6$, $1 \times 10^7$, $5 \times 10^7$, and $8 \times 10^7$ to about $5 \times 10^8$, $5 \times 10^7$, $1 \times 10^8$, $5 \times 10$ $1 \times 10$ and $1 \times 10^{10}$ and/or any combination thereof.

In one embodiment the article has a flexural stiffness of less than about 10 grams/cm, in another embodiment less that about 5 grams/cm, in another embodiment less that about 3 grams/cm, in another embodiment less than about 2 grams/cm and in yet another embodiment from about 0.1, 0.5, 1, to about 2, 3, 5, 10 grams/cm, in any combination, flexural stiffness as measured on a Handle-O-Meter, model #211-300, available from Thwing-Albert Instrument Company of Philadelphia, Pa. as per test method ASTM D2923-95.

In one embodiment the articles herein have a normalized dislodgement force of from about 1100 to about 12,000 grams per sq.cm, in another embodiment from about 1300 to about 10,000 grams per sq.cm, in another embodiment from about 1200 to about 5000 grams per sq.cm, in another embodiment from about 1400 to about 5000 grams per sq.cm, in another embodiment from about 1300 to about 2500 grams per sq.cm, in another embodiment from about 1750 to about 2500 grams per sq.com. In another embodiment the normalized dislodgement force is from about 1100, about 1200, about 1300, about 1400, about 1500, about 1750 grams per sq.cm. to about 12,000, about 10,000, about 7500, about 5000, about 2500, about 2250 grams per sq.cm, and/or any combination thereof. In one embodiment the dislodgement force ratio is from about 1.1, 1.2, 1.3, 1.4, 1.5, 1.6, 1.7, 1.8, 1. 2.0 to about 1.3, 1.4, 1.5, 1.6, 1.7, 1.8, 1. 2.0, 3, 4, 5, 6, 8, 10, and/or any combination thereof. In one embodiment the dislodgement force ratio is from about 1.1 to about 10, from about 1.1 to about 8, from about 1.3 to about 4, and/or from about 1.3 to about 2.5.

In one embodiment the articles herein are substantially solid prior to use and can be picked up manually, in substantially one piece, and positioned on the denture. Additionally, in one embodiment the articles are capable of being picked up manually, and positioned on the denture, resulting in little or no residue on the fingers. In another embodiment the articles comprise a single layer. In yet another embodiment the articles are laminates and/or composites. In one embodiment the articles are pre-shaped and/or preformed. In another embodiment the articles herein may be dispensed by the consumer via a unit dose package, multi-dose package, pump, sachet, syringe, or tube, and shaped by the consumer; and in yet another embodiment the articles may be shaped by the consumer without leaving a substantial residue on their hands.

In one embodiment, the denture adhesive article is sufficiently flow-able to allow it to be applied from a tube and subsequently picked up and positioned on the denture. In one embodiment, the denture adhesive article is sufficiently flow-able to allow it to be applied from a tube and subsequently picked up, and positioned on the denture, with little/no residue on the fingers. In another embodiment the denture adhesive article comprises a solvent which results in an article that is sufficiently flow-able to be applied from a tube. The solvent may be subsequently dissipated, by evaporation, bio-absorption, dispersion, dissolution, etc. In another embodiment the above mentioned optional solvent is also miscible with the water soluble component. In one embodiment, the denture adhesive article is sufficiently flow-able to allow it to be applied from a tube and only minimally ooze out from under the denture. In one embodiment the denture adhesive article has a "normalized ooze amount" from about 0%, 0.00001%, 0.001%, 5%, 10%, 15%, 20%, 25%, 30% to about 15%, 20%, 25%, 30%, 40%, 50% and/or any combination thereof. In one embodiment the denture adhesive article has a "ooze ratio" from about 0, 0.00001, 0.001, 0.01, 0.1, 0.2, 0.3, 0.4, 0.5, 0.6 to about 0.3, 0.4, 0.5, 0.6, 0.7, and/or any combination thereof Regardless of the form of dispensing the article, including but not limited to pre-dosed ready to use articles and/or articles which are dispensed such as from a tube, the articles are substantially solid prior to use and can be picked up manually. Denture adhesive articles that can be dispensed from a tube can be identified as articles by the following method:

Please read all steps before starting test.

1. Fill product into a tube with a 0.16" diameter nozzle.
2. Extrude a 1" long strip of product onto a denture tile (1.5"×1.5" square tile made from denture-plastic) taking care to hold the nozzle about ⅛" above the denture-tile. Do not touch the nozzle to denture-tile while extruding the product.
3. After about 1" of product has been extruded, hold nozzle about ⅛" above the denture-tile and use a spatula to cut the strip against the nozzle. Do not touch or smear the nozzle against the denture-tile while cutting strip.
4. Use thumb and forefinger to hold the middle of the strip and pick it up vertically off the denture-tile. Do not use a wiping motion of the fingers against the denture-tile.
5. The composition is an article if it can be picked up in substantially one piece.

Some denture adhesive articles are pre-dosed and/or ready to use. A user may be able to identify these items visually as a denture adhesive article, as they are often in the form of a strip contained within a package. However, if not evident that these denture adhesive products are articles, these denture adhesive articles can be identified as articles by the following method:

1. Shape composition into a sheet about 0.67 mm thick× about 8 mm wide×about 44 mm long.
2. Place sheet on a denture-tile.
3. Use fingers to pick up sheet.
4. The composition is an article if it can be picked up in substantially one piece.

Substantially in one piece means, as used herein, that from about 75, 80, 85, 90% to about 100, 90, 85, 80, 75, 70% and/or any combination thereof of the denture adhesive composition remains in one piece when manually picked up from the denture surface.

In addition to the aforementioned test methods denture adhesive articles can also be identified as articles by the amount of ooze, as determined by the ooze method (as defined herein). In addition to being able to be manually picked up and moved in substantially one piece, a denture adhesive article has a normalized ooze amount of from about 0, 3, 5, 10, 15, 20, 25% of the total composition to about 30, 25, 20, 15, 10, 5, 3% of the total composition and/or any combination thereof and/or the ooze ratio is from about 0, 00001, 0.001, 0.01, 0.1, 0.2, 0.25, 0.3, to about 0.1, 0.2, 0.25, 0.3, 0.4, 0.5 and/or any combination thereof.

In one embodiment the article herein comprises ingredients of natural origin.

In one embodiment the article herein comprises a homogeneous mixture.

DENTURE ADHESIVE COMPONENT

The present invention comprises a safe and effective adhesive amount of a denture adhesive component, generally at a level of from about 10% to about 90%, in another embodiment from about 15% to about 70%, in another embodiment from about 20% to about 70%, in yet and in another embodiment from about 25% to about 65%, and in yet another embodiment from about 30% to about 65%, by weight of the article. In one embodiment the articles of the present invention comprise from at least 20 percent by weight, and in another embodiment at least 30 percent by weight of the article, of a denture adhesive component.

In one embodiment the denture adhesive components herein are mucoadhesive, hydrophilic, water soluble, have the property of swelling upon exposure to moisture, and/or to form a mucilaginous mass when combined with moisture. In one embodiment the denture adhesive components are selected from the group consisting of natural gums, synthetic polymeric gums, AVE/MA, salts of AVE/MA, AVE/MA/IB, salts of AVE/MA/IB, copolymer of maleic acid or anhydride and ethylene and salts thereof, copolymer of maleic acid or anhydride and styrene and salts thereof, copolymer of maleic acid or anhydride and isobutylene and salts thereof, polyacrylic acid and polyacrylates thereof, polyitaconic acid and salts thereof, mucoadhesive polymers, water-soluble hydrophilic colloids, saccharide derivatives, cellulose derivatives, and mixtures thereof. Examples of such materials include karaya gum, guar gum, gelatin, algin, sodium alginate, tragacanth, chitosan, acrylamide polymers, carbopol, polyvinyl alcohol, polyamines, polyquarternary compounds, polyvinylpyrrolidone, cationic polyacrylamide polymers, AVE/MA, AVE/MA/IB, mixed salts of AVE/MA, mixed salts of AVE/MA/IB, polymeric acids, polymeric salts, polyhydroxy compounds, and mixtures thereof.

In one embodiment the denture adhesive components are selected from the group consisting of salts of AVE/MA, mixed salts of AVE/MA, cellulose derivatives (such as methylcellulose, carboxymethylcellulose, hydroxyethylcellulose, hydroxypropylcellulose, hydroxy-propylmethylcellulose, and mixtures thereof), polyethylene glycol, karaya gum, sodium alginate, chitosan, corn starch, and mixtures thereof. In yet another embodiment, the adhesive component is selected from the group consisting of mixed salts of AVE/MA, cellulose derivatives, and mixtures thereof.

In one embodiment the denture adhesive component is not thermoplastic and/or comprises only low levels of water soluble thermoplastic polymers, from about 0.01 to about 5% of water soluble thermoplastic polymer such as polyethylene oxide, hydroxypropyl cellulose, hydroxyproplymethylcellulose; polyethylene glycol; in another embodiment from about 0.01 to about 1% of water soluble thermoplastic polymer, or is essentially free of water soluble thermoplastic polymers.

Alkyl Vinyl Ether-Maleic Copolymer

In one embodiment of the invention the denture adhesive component is AVE/MA or salts of AVE/MA. The alkyl vinyl ether-maleic acid co-polymer comprises or consists essentially of the repeated structural unit:

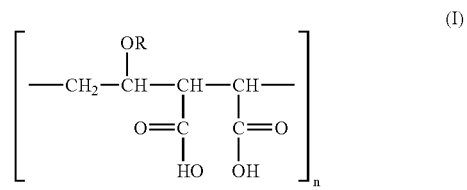

(I)

wherein R represents an alkyl radical, in one embodiment a $C_1$ to $C_5$ alkyl radical, n is an integer greater than one representing the number of repeated occurrences of the structural unit in a molecule of the polymer.

In one embodiment, the adhesive component is AVE/MA and salts thereof, preferably mixed salts of AVE/MA, wherein the copolymer contains a cationic salt function comprising a cation selected from the group consisting of Group IA and Group 2A cations of the periodic table, yttrium, titanium, zirconium, vanadium, chromium, manganese, iron, nickel, copper, zinc, boron, aluminum, and mixtures thereof. In another embodiment, the adhesive component is a mixed salt of AVE/MA containing a cationic salt function comprising a cation selected from the group consisting of strontium, zinc, iron, boron, aluminum, vanadium, chromium, manganese, nickel, copper, yttrium, titanium, magnesium, calcium, sodium, and mixtures thereof, and in yet another embodiment the cation is selected from the group consisting of strontium, zinc, iron, magnesium, calcium, sodium, and mixtures thereof.

AVE/MA contains, in one embodiment, a cationic salt function comprising from about 5% to about 50%, in another embodiment, from about 10% to about 40%, in yet another embodiment, from about 10% to about 35% (of the total initial carboxyl groups reacted) zinc cations. These zinc cations can be mixed with other cations selected from the group consisting of: from about 5% to about 65%, preferably from about 10% to about 60%, strontium cations, from about 0.001% to about 2.5%, preferably from about 0.01% to about 2% of iron, boron, aluminum, vanadium, chromium, manganese, nickel, copper, yttrium, and/or titanium cations, from about 5% to about 65%, preferably from about 15% to about 50% of calcium and/or magnesium cations and/or sodium cations.

AVE/MA and salts thereof, are also described in U.S. Pat. No. 5,073,604 to Holeva et al., issued Dec. 17, 1991; U.S. Pat. No. 5,525,652, issued Jun. 11, 1996, Clarke et al.; U.S. Pat. No. 6,025,411, issued Feb. 15, 2000, Wong et. al.; U.S. Pat. No. 4,758,630, issued Jul. 1 1988, Shah et al.; U.S. Pat. No. 5,304,616, issued Apr. 1, 1994, Rajaiah et al.; U.S. Pat. No. 5,424,058, issued Jun. 13, 1995, Rajaiah; U.S. Pat. No. 5,424, 058, issued Jun. 13, 1995, Rajaiah et al.; U.S. Pat. No. 4,758, 630, issued Jul. 1, 1988, Shah et al.; U.S. Pat. No. 5,830,933, issued Nov. 3, 1998, Synodis et al.; U.S. Pat. No. 2,047,398, issued Jul. 14, 1936, Voss et al.; U.S. Pat. No. 3,003,988, issued Oct. 10, 1961, Germann et al.; U.S. Pat. No. 5,880,172, Rajaiah et al., issued March 1999; U.S. Pat. No. 5,900,470, Prosise et al., issued May 4, 1999; U.S. Pat. No. 5,037,924, Tazi et al., issued Aug. 6, 1991; U.S. Pat. No. 5,082,913, Tazi et al, issued Jan. 21, 1992; all of which are incorporated herein by reference in their entirety. Salts of AVE/MA are also described in P&G copending applications U.S. Pat. No. 6,355,706 to Rajaiah, et al., issued Mar. 12, 2002; U.S. Pat. No. 6,617,374 to Rajaiah, et al., issued September, 2003.

In one embodiment the free acid level of the salts of the AVE/MA or AVE/MA/IB is at least about 36%, in another embodiment is from about 36% to about 60%, and even in another embodiment is from about 40% to about 55%, of the total initial carboxyl groups of the copolymer.

In one embodiment the specific viscosity of the starting copolymer acid or copolymer anhydride is from about 1.2 to about 14, when preferably measured in a 1% weight/volume solution in MEK (methyl ethyl ketone) at 25° C. Other methods and solvents can be used to measure the specific viscosity such as a 1% weight/volume solution in DMF (dimethyl formamide) at 25° C. and a 1% weight/volume solution in 2-butanone at 25° C.

Suitable AVE/MA copolymers may be prepared by well-known methods of the prior art; see, for example, U.S. Pat. No. 2,782,182, and U.S. Pat. No. 2,047,398.

Methods of making mixed salts of AVE/MA polymers are further disclosed in U.S. Pat. No. 5,073,604, Holeva et al., issued Dec. 17, 1991 and U.S. Pat. No. 5,872,161, Liang et al., issued Feb. 16, 1999.

WATER SOLUBLE PLASTICIZER OR CARRIER

The articles of the present invention comprise a safe and effective amount of one or more water soluble, toxicologically-acceptable plasticizers and/or water soluble carriers. In one embodiment the level of the plasticizing agent or carrier ranges from about 0.1, 1, 2, 5, 10, 20% to about 10, 20, 40, 80% in any combination of the ranges. Suitable plasticizing agents or carriers of the present invention include, but are not limited to, ethanolamines; ethylene glycol; polyethylene glycol; polyethylene oxide; glycerol; propylene glycol; 1,2,6-hexanetriol; triacetin; diacetin; monoacetin; 1,5-pentanediol; trimethylolpropane; polyols (such as sorbitol); glycerin; water; acetylated monoglyceride; hydrogenated starch hydrolysates; corn syrups; and derivatives thereof; xylitol, glycerol monoesters with fatty acids; dimethyl phthalate; diethyl phthalate; dioctyl phthalate; diethylene glycol; triethylene glycol; tricresyl phosphate; dimethyl sebacate; ethyl glycolate; ethylphthalyl ethyl glycolate; o- and p-toluene ethyl sulfonamide; hydroxyl propyl cellulose; hydroxyl propyl methyl cellulose; polyvinyl alcohol; alcohol; polymeric alcohol; polymeric acid; ethanol; propanol; water; and mixtures thereof.

In another embodiment the plasticizer or carrier is selected from the group consisting of ethanolamines; ethylene glycol; polyethylene glycol; polyethylene oxide; glycerol; propylene glycol; 1,2,6-hexanetriol; triacetin; diacetin; monoacetin; 1,5-pentanediol; trimethylolpropane; hydroxyl propyl cellulose; hydroxyl propyl methyl cellulose; polyvinyl alcohol; alcohol; polymeric alcohol; polymeric acid; ethanol; propanol; water; and mixtures thereof.

In one embodiment the article comprises from about 10, 20, 30% to about 40, 50, 60%, in any combination, of plasticizer or carrier, having a dry tack of from about 0.025, 0.05, 0.1, 1, 5, 10 gram-force/square centimeter to about 0.5, 1, 5, 10, 100, 1000, 10,000 gram force/square centimeter, in any combination of these ranges.

In one embodiment the article is substantially free of esterified copolymer of methylvinylether-maleic anhydride, hydrophobic acetate, acrylic ester derivative, polyvinyl acetate, Polybutene, silicone, rubber, paraffin wax, polyethylmethacrylate, polymethyl methacrylate, organo soluble cellulose, triacetin, butyl phthalyl butyl glycolate, phthallic acid derivatives or combinations thereof. In one embodiment the article is substantially free of polyethylmethacrylate, triacetin, or combinations thereof.

In one embodiment, the denture adhesive article, when extruded thermoplastically, does not cure and set as a result of the action of the plasticizer component. In another embodiment the plasticizer component does not solidify the water soluble component or the denture adhesive article.

In one embodiment, the article is substantially free of plasticizers.

ADDITIONAL INGREDIENTS

Gellant Agents

The articles of the present invention may also optionally comprise a safe and effective amount of one or more toxicologically-acceptable gellants. In one embodiment the level of the gellant agent ranges from about 0.01% to about 40%, in another embodiment from about 1% to about 10%, in another embodiment from about 2% to about 5%, by weight of the article.

Suitable gellant agents of the present invention include, but are not limited to, polyvinylpyrrolidone/eicosene copolymer sold under the tradename Ganex V-220F from ISP; tricontanyl polyvinylpyrrolidone sold under the tradename Ganex WP-660 from ISP; polyamide gallants including Sylvaclear, Sylvacote, Sylvagel, Uniclear all available from Arizona Chemical including Sylvaclear Lightwax; Sylvaclear PA 20; Sylvaclear PA 30; Sylvaclear PA 50; Sylvacote 2228; Sylvacote 2228E; Sylvagel 5000; Sylvagel 6000; Uniclear 100; Uniclear 100VG; Uniclear 80; Uniclear 80V; and mixtures thereof.

Flavors, Fragrance, Sensates

The articles of the present invention may also include one or more components which provide flavor, fragrance, and/or sensate benefit (warming or cooling agents). Suitable components include menthol, wintergreen oil, peppermint oil, spearmint oil, leaf alcohol, clove bud oil, anethole, methyl salicylate, eucalyptol, cassia, 1-8 menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof, as well as coolants. The coolant can be any of a wide variety of materials. Included among such materials are carboxamides, menthol, ketals, diols, and mixtures thereof. In one embodiment the coolants in the present articles are selected from the group consisting of the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haannann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,45425, Amano et al., issued Aug. 10, 1984. WS-3 and other agents are described in U.S. Pat. No. 4,136,163, Watson, et al., issued Jan. 23, 1979. These agents may be present at a level of from about 0% to about 40%, in another embodiment from about 0.05 to about 5%, and in another embodiment from about 0.1 to about 2%, by weight of the article.

Other Optional Ingredients

The denture adhesive articles may also comprise one or more therapeutic actives suitable for topical administration. Therapeutic actives may be present at a level of from about 0% to about 70%, by weight of the article, and in one embodiment from about 1% to about 20% by weight of the article. Therapeutic actives include antimicrobial agents such as iodine, triclosan, peroxides, sulfonamides, bisbiguanides, or phenolics; antibiotics such as tetracycline, neomycin, kanamycin, metronidazole, cetylpyridium chloride, domiphen bromide, or clindamycin; anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; fluorides such as sodium fluoride, stannous fluoride, MFP; anesthetic agents such as lidocaine or benzocaine; anti-fungals such as those for the treatment of *candida albicans*; aromatics such as camphor, eucalyptus oil, and aldehyde derivatives such as benzaldehyde; insulin; steroids; herbal and other plant derived remedies; and baking soda. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

Other suitable ingredients include colorants, preservatives (such as methyl and propyl parabens), thickeners such as silicon dioxide, and polyethylene glycol. Colorants, preservatives, thickeners may be present at levels of from about 0% to about 20%, by weight of the article, in another embodiment from about 0.1% to about 10%, by weight.

Additionally, the articles may also comprise one or more solvents. These optional solvents may be miscible with the water soluble component and/or be capable of being dissipated in-situ. In one embodiment these solvents may be dissipated in-situ by evaporation, dissolution, dispersion, bioabsorption, or any other suitable means. In another embodiment these solvents may be dissipated in-situ to leave behind a denture adhesive article. Such solvents may include materials with a viscosity ranging from 0.01, 0.1, 1, 5 centipoise 20° C., to 5, 10, 100, 1000 centipoise at 20° C. in any combination of these levels. In one embodiment these solvents may be silicones, hydrocarbons, iso-dodecane, isohexadecane, iso-eicosane, and/or polyisobutene. Suitable grades of solvents include the Permethyl series (sold by Prespers Inc., N.J.) such as Permethyl 97A, 99A, 101A, 102A, and mixtures thereof.

PROCESS FOR PREPARATION OF THE ARTICLE

Process for Preparation of the Article

In one embodiment the articles utilized in accordance with the invention are formed by processes conventional in the arts, e.g. the film making industries such as casting, coating, calendaring, extrusion. In one embodiment the separate components of the article are melted and then blended in a mixing tank until a homogeneous mixture is achieved. Thereafter, the melted mixture may be cast to an acceptable thickness, on an appropriate substrate. Examples of such substrates include Mylar, continuous moving stainless steel belt (which may eventually entering a dryer section if needed), release paper and the like. The articles are then cooled. The articles may then be dried if needed, e.g. in a forced-air oven. The temperature of the drying air and length of drying time depend on the nature of the solvent utilized as is recognized in the art. Generally, the drying temperatures include a temperature between about 25° C. and 140° C., in another embodiment from about 60° and 90° C. for a duration of about 20 minutes to about 60 minutes, in another embodiment from about 30 to about 40 minutes. The article may then be cut into desired shapes with desired dimensions and then stacked and/or subsequently individually packaged.

In one embodiment, after processing, the article is then die-cut into desired shapes. These shapes may facilitate application of the article to the dentures.

In one embodiment in particular the present article is processed as follows:

1. Dissolve the denture adhesive component such as CMC and a plasticizer such as Glycerin into a solvent such as water or alcohol, 2. Cast the resulting solution/dispersion onto a flat surface, 3. Allow the solvent to evaporate (with heat if needed), 4. Remove from substrate or mold or cut into the desired shape.

Another conventional film-making process known in the art is extrusion. This method is possible with films wherein the film forming ingredient comprises a variety of extrudable materials. The mechanical particulars of the extrusion process, e.g. the particular equipment utilized, the extruding force, the shape and temperature of the orifice and/or dies are considered to be within the skill of the art and can be varied in a known manner to achieve the physical characteristics of the articles described herein.

In one embodiment the thickness of the articles herein is generally between about 0.1 mm to about 2.5 mm, in another embodiment is from about 0.4 mm to about 1.5 mm thick, in another embodiment is from about 0.5 mm to about 1mm thick. The article may be thicker or thinner depending on the degree of cushioning desired by the user or wearer.

In one embodiment the articles herein may optionally be multiphase or have visually distinct phases. In another embodiment the articles herein may optionally have a release liner.

ARTICLE USE

The present articles are generally applied to the denture prosthesis and thereafter the denture is secured to the oral cavity. In one embodiment the dentures are dried prior to application of the article. In one embodiment it is not necessary to wet the article and/or the denture prosthesis prior to applying it to the denture prosthesis in order to make the article stick to the denture prosthesis. The article may be applied to any suitable location on the prosthesis. In one embodiment the denture wearer generally wears the article from about 1 hour to about 3 days, in another embodiment from about 6 hours to about 24 hours. After usage the prosthesis is removed from the oral cavity, and any remaining article may be cleaned from the prosthesis, for example by gentle scrubbing with water and a brush.

The following examples further describe and demonstrate embodiments within the scope of the present invention. The examples are given solely for the purpose of illustration and are not to be construed as limitations of the present invention. Many variations of these are possible without departing from the spirit and scope of the invention.

EXAMPLES

Example I

| Sample | PEG 600 | PEG 1000 | CMC 7HF | Ca/Zn Gantrez | Carageenan | Xanthan |
|--------|---------|----------|---------|---------------|------------|---------|
| A      | 11.75   | 35.25    |         |               |            | 53      |
| B      | 11.75   | 35.25    |         |               | 53         |         |
| C      | 11.75   | 35.25    | 20      | 33            |            |         |
| D      | 9.4     | 37.6     | 20      | 33            |            |         |
| E*     | 35.25   | 11.75    | 20      | 33            |            |         |
| F*     | 4.7     | 42.3     | 20      | 33            |            |         |

*Examples E & F are for comparative purposes only

The above formulas can be made by the following procedure: PEG 1000 is heated at approximately 50 C. on a hot plate to melt it. The molten PEG 1000 is then mixed with the appropriate amount of PEG 600 (a liquid at room temperature). While still warm, the molten solutions is mixed with CMC, Gantrez, Carregeenan, and/or Xanthan gum depending on the specific formulation. After mixing, the formulations are pressed at room temperature under 9000 lb of pressure for approximately 2 minutes. The samples are then removed from the press and in one embodiment evaluated for dry tack.

Example II

| Sample | CMC 7LF | Glycerin | DI H2O |
|--------|---------|----------|--------|
| A      | 0.1     | 0.05     | 9.85   |
| B      | 0.1     | 0.1      | 9.8    |
| C*     | 0.1     | 0        | 9.9    |
| D*     | 0.1     | 0.25     | 9.65   |

*Examples C & D are for comparative purposes only

The above formulas can be made by the following procedure: CMC are mixed with water and glycerin on a stir plate with high magnetic stirring to create a vortex. After approximately 20 minutes of stirring to allow the CMC to dissolve, the samples are cast onto Teflon boats. The samples are then placed in an oven under vacuum at approximately 50 C. overnight to remove water. The samples are then removed from the Teflon boats and in one embodiment evaluated for dry tack.

TEST METHODS

The bioerosion of the inventive articles can be measured by the following method: run a water source on top of the sample specimen for about 30 minutes while the specimen sits atop a wire mesh. The water source is a laboratory faucet adjusted such that the temperature is 39±1° C. and the flow rate is 16±1 ml/sec. Use a funnel to focus the flow and help dampen the effect of small pressure and temperature fluctuations within the water lines. The wire mesh grid has square openings approximately 0.09 inches×0.09 inches and is placed 2.5 inches below the tip of the funnel where it is clamped to a metal ring for support. Sample specimens weighing 0.025 g are placed on the mesh and images are taken at 0, 10 and 30 minutes to follow bio-erosion of the specimen. After 30 minutes the wire mesh containing the remainder of the specimen is removed and heated for 1 hour at 60° C. under vacuum to remove all remaining water. After the heating period, final weights are taken to calculate weight loss due to bio-erosion. An average of 3 specimens per sample are used to calculate bio-erosion time and weight loss. The article is bioerodible if it does not leave behind visible residue, film, or sheet after about 30 minutes under these testing conditions., and/or if it cannot be easily separated or peeled away manually in one or more large pieces after about 30 minutes under these testing conditions, and/or if it leaves behind less than about 2, less than about 4, less than about 6, and/or less than about 8% by weight of residue (of the original weight of the article) after about 30 minutes under these testing conditions. The above bio-erosion test may also be conducted at various time-points up to 8 hours.

The dry tack can be measured by the following method: 1. remove the article from the package material; 2. place the article on the palate-portion of a dry, acrylic upper-denture with the teeth facing downward; 3. apply pressure with fingers for about 3 to 10 seconds; 4. thereafter remove finger pressure; 5. then invert the denture with the teeth facing upward. In one embodiment the article demonstrates dry tack if: i. The article does not stick to fingers during steps 1-2, ii. leaves little or no residue on the fingers in steps 3-4, and iii. in step-5, the article does not fall off of the denture, once inverted, for at least about 10-30 seconds, or at least about 1 minute.

In another embodiment the article demonstrates dry tack if: i. The article does not stick to fingers during steps 1-4, and ii. in step-5, the article does not fall off of the denture, once inverted, for at least about 10-30 seconds, or at least about 1 minute.

In another embodiment the article demonstrates dry tack if in step-5, the article does not fall off of the denture, once inverted, for at least about 10-30 seconds, or at least about 1 minute.

The dry tack of the inventive articles can also be measured by the following procedure:

a. Compress a 5 mm diameter disc (0.67 mm thick) sample of the article between a 1" diameter cylindrical probe (made from polymethylmethacrylate) and a flat sheet of polymethylmethacrylate with a 2000 gram-force for 2 seconds, b. Pull off the probe at 1 mm/second and record peak force, c. Repeat procedure with no sample sandwiched between the two surfaces, and d. Calculate: Dry Tack in grams/square centimeter=(Peak Force with Sample-Peak Force without sample)/Cross sectional area of sample disc.

In one embodiment the above procedure is repeated with an applied force of 250 gram-force in step-a and the tack measured in steps b-d;

The article has dry tack if the tack measured with a 250 gram-force applied force is less than about 25, 50, 100, 200, or 500 grams/square-centimeter, and the tack measured with a 2000 gram-force applied force is greater than about 200, 500, 1000, 2000, 5000, 10000, or 25000 grams/square-centimeter, and any combination of these levels.

The modulus G' of the inventive article can be measured by the following procedure:

a. Load a sample disc of 8 mm diameter and 0.67 mm thickness onto a ARES rheometer using a parallel plate fixture with a compressive force of 500 grams. If the sample is flowable, a sufficient amount of material is used to fill the 1 mm gap on a 25 mm diameter parallel plate fixture.

b. Set strain to be 0.02%, c. Measure G' at a sweep of frequencies including 1 Hz.

The normalized dislodgement force and dislodgement force ratio of the inventive article can be measured by the following method:

Instrument: An Instron model 5544 is used. The load cell is calibrated according to manufacturer's specifications annually. The choice of load cell is determined by having the forces generated by the adhesive fall within the recommended operating range for the load cell. This is typically between 10%-90% of full capacity.

Test Fixtures: The geometry of a cylindrical probe and a flat plate are used as the test fixtures. The probe is made from PMMA, 0.2 sq.cm to 10 sq.cm in surface area. For the base plate, the same PMMA material is used but in sheet form, ¼" thick. This is cut into 6"×6" plates to be clamped onto the Instron.

Hydrating Liquid: Artificial saliva containing low levels of various salts is used to hydrate the adhesive.

| Artificial Saliva Composition | |
|---|---|
| Ingredient | Amount per Liter |
| $K_2HPO_4$ | 4.2 g |
| $KH_2PO_4$ | 3.2 g |
| KOH | 2 pellets |
| Mineral Stock Solution | 5 ml |
| KCl | 8 g per 100 ml of Stock Solution |
| NaCl | 8 g |
| $Na_2SO_4$ | 0.264 g |
| $MgCl_2 \cdot 6H_2O$ | 0.7687 (or 0.36 g Anhydrous $MgCl_2$) |

Adhesive: 0.1 to 1.0 gram of adhesive is applied to the probe.

Hydration: The hydrating liquid (0.2 mL of artificial saliva to 2.0 ml) is pipetted onto the surface of the adhesive. The assembly is then permitted to hydrate for 20 minutes or more.

Test Method: Once the sample is hydrated, it is mounted onto the Instron and the test is carried out via computer control. The method is comprised of the following steps:

(a) Compression to 750 to 7500 g of force
(b) Hold at compression for 2 minutes
(c) Reduce compressive force to 200 gf
(d) Hold (1 minute)
(e) Pull off at 1 mm/s
(f) Record Peak Dislodgement Force
(g) Calculate "Normalized Dislodgement Force"=(Peak Dislodgement Force)/(Surface Area of Probe); report in grams force per sq.cm
(h) Repeat steps A-F for commercial Fixodent Original denture adhesive (available commercially manufactured by P&G), or for the following reference formula:

Ca(47.5%)/Zn(17.5%) MVE/MA salt 33%, sodium carboxymethylcellulose 20%, mineral oil USP (65-75cst at 40C.) 23.93%, petrolatum USP (consistency 17-20 mm) 21.87%, colloidal silicon dioxide 1.14%, and Opatint OD1646 0.06%; suitable methods to make this reference formula are disclosed in U.S. Pat. No. 5,073,604, Holeva K., and U.S. Pat. No. 6,617, 374 Rajaiah J.

(i) Calculate "Dislodgement Force Ratio"=(Peak Dislodgement Force of Prototype Adhesive)/(Peak Dislodgement Force of Fixodent Original)

Data: Each sample is repeated a minimum of 3 times and the average value of the "Normalized Dislodgement Force" and "Dislodgement Force Ratio" are reported.

Specifically the normalized dislodgement force and dislodgement force ratio can be measured by using the following parameters in the procedure: 0.25 gram adhesive; 1 inch diameter probe; hydration time of 20 minutes; and compression force of 7500 grams.

The "normalized ooze amount" and "ooze ratio" of the inventive article can be measured by the following procedure:

a. Load initial sample weight of about 0.50 grams uniformly onto a 1 inch diameter cylindrical probe made from polymethylmethacrylate,
b. Bring probe to 1.2 mm of base plate, also made from polymethylmethacrylate,
c. Apply 750 gram force for 90 seconds,
d. At 90 seconds, trim and weigh material that has oozed out,
e. Calculate "Normalized Ooze Amount"=(Amount oozed out/Initial sample weight)×100,
f. Repeat Steps a-e using commercial Fixodent Original a denture adhesive cream commercially manufactured by P&G, or with the following reference formula:

Ca(47.5%)/Zn(17.5%) MVE/MA salt 33%, sodium carboxymethylcellulose 20%, mineral oil USP (65-75cst at 40C.) 23.93%, petrolatum USP (consistency 17-20 mm) 21.87%, colloidal silicon dioxide 1.14%, and Opatint OD1646 0.06%; suitable methods to make this reference formula are disclosed in U.S. Pat. No. 5,073,604, Holeva K., and U.S. Pat. No. 6,617,374 Rajaiah J., g. Calculate "Ooze Ratio"=Normalized Ooze Amount of Prototype Adhesive/ Normalized Ooze Amount of Fixodent Original,
h. Each sample is repeated a minimum of 3 times and the average value of the "Normalized Ooze Amount" and "Ooze Ratio" are reported.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A denture adhesive article, comprising:
a) about 65% to about 90% by weight of a water soluble denture adhesive component selected from the group consisting of: saccharide derivatives, natural gums, and mixtures thereof;
b) about 5% to about 15% by weight of a water soluble plasticizer selected from the group consisting of: polyethylene glycol, glycerin, and mixtures thereof; and c) about 0.1% to about 45% by weight of a carrier selected from the group consisting of: water, polyethylene glycol, and mixtures thereof;

wherein the article has dry tack.

2. The article of claim 1, wherein the saccharide derivative is selected from the group consisting of: carrageenan, xanthan gum, and mixtures thereof.

3. The article of claim 1, wherein the water soluble denture adhesive component further comprises AVE/MA and the total amount of the water soluble denture adhesive is still between about 65% and about 90% by weight.

4. The article of claim 3, wherein the water soluble denture adhesive consists essentially of about 15% to about 25% by weight of carrageenan and about 25% to about 45% by weight of AVE/MA.

5. The article of claim 3, wherein the AVE/MA is a mixed salt AVE/MA.

6. The article of claim 1, wherein the carrier comprises water, the plasticizer comprises glycerin, and the adhesive comprises carrageenan.

7. The article of claim 6, wherein the article is formed by evaporating away the water.

8. The article of claim 1, wherein the plasticizer comprises polyethylene glycol and the carrier comprises a higher molecular weight polyethylene glycol.

9. The article of claim 8, wherein the plasticizer comprises polyethylene glycol with an average molecular weight of about 600 and the carrier comprises polyethylene glycol with an average molecular weight of about 1000.

10. The article of claim 8, wherein the water soluble denture adhesive comprises carrageenan.

11. The article of claim 8, wherein the water soluble denture adhesive comprises xanthan.

* * * * *